US006249590B1

United States Patent
Young et al.

(10) Patent No.: US 6,249,590 B1
(45) Date of Patent: Jun. 19, 2001

(54) METHOD FOR AUTOMATICALLY LOCATING IMAGE PATTERN IN DIGITAL IMAGES

(75) Inventors: Susan S. Young, Buffalo; Hsien-Che Lee, Penfield, both of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/243,400

(22) Filed: Feb. 1, 1999

(51) Int. Cl.[7] .................................................. G06K 9/00
(52) U.S. Cl. ........................................... 382/103; 348/169
(58) Field of Search ........................... 382/103, 28, 133; 356/401; 701/301; 348/169

(56) References Cited

U.S. PATENT DOCUMENTS

| | | | |
|---|---|---|---|
| 4,851,984 | 7/1989 | Doi et al. | 382/108 |
| 4,922,915 | 5/1990 | Arnold et al. | 382/128 |
| 4,951,201 | 8/1990 | Takeo et al. | 382/128 |
| 5,228,068 | 7/1993 | Mazess | 378/54 |
| 5,268,967 | 12/1993 | Jang et al. | 382/132 |
| 5,341,439 | * 8/1994 | Hsu | 382/28 |
| 5,875,258 | * 2/1999 | Ortyn et al. | 382/133 |
| 5,983,161 | * 11/1999 | Lemelson | 701/301 |
| 6,130,750 | * 10/2000 | Ausschnitt et al. | 356/401 |

OTHER PUBLICATIONS

D.T. Morris et al., "Segmentation of the finger bones as a prerequisite for the determination of bone age," *Image and Vision Computing*, vol. 12, No. 4, pp. 239–246, May 1994.

E. Pietka et al., "Feature extraction in carpal–bone analysis," *IEEE Transactions on Medical Imaging*, vol. 12, No. 1, pp. 44–49, 1994.

E. Pietka et al., "Computer–assisted phalangeal analysis in skeletal age assessment," *IEEE Transactions on Medical Imaging*, vol. 10, No. 4, pp. 616–619, Dec. 1991.

C.–L. Chang et al., "Computer–aided diagnosis: detection and characterization of hyperparathyroidism in digital hand radiographs," *Medical Physics*, 20(4), pp. 983–992, Jul./Aug. 1993.

P.P. Smyth et al., "Automatic measurement of vertebral shape using active shape models," *Proceedings of British Machine Vision Conference*, Edinburge, Sep. 9–12, 1996.

J.M. Muggleton et al., "Automatic location of vertebrae in digitized videofluoroscopic images of the lumbar spine," *Medical Engineering and Physics*, vol. 19, No. 1, pp. 77–89, 1997.

M.P. Chwialkowski et al., "Automated localization and identification of lower spinal anatomy in Magnetic Resonance images," *Computers and Biomedical Research*, 24(2), pp. 99–117, 1991.

G. Taascini et al., "Automatic quantitative analysis of lumbar bone–radiographs," *Proceedings of the 1993 IEEE Nuclear Science Symposium & Medical Imaging Conference*, vol. 3, pp. 1722–1726, San Francisco, CA, Oct. 30–Nov. 6, 1993.

* cited by examiner

Primary Examiner—Joseph Mancuso
Assistant Examiner—Abolfazl Tabatabai
(74) Attorney, Agent, or Firm—William F. Noval

(57) ABSTRACT

A method for automatically locating instances of a target pattern in digital images, comprising the steps of: providing a digital image; detecting a first simple feature associated with the target patterns in the digital image; for each detected feature, searching, in its spatial neighborhood, a second or a plural of other features associated with the target patterns; for each pair of plural of features detected, checking the consistency of image intensity profile with the target pattern within the spatial neighborhood as delimited by the feature points detected in the searching and detecting steps; and labeling those image regions that are found to be consistent with the structure of the target pattern in the checking step.

4 Claims, 13 Drawing Sheets

FIG. 4a

| -.17 | -.41 | -.32 | .44 | (1.00) | .44 | -.32 | -.41 | -.17 |
|---|---|---|---|---|---|---|---|---|
| -.17 | -.41 | -.32 | .44 | (1.00) | .44 | -.32 | -.41 | -.17 |
| -.17 | -.41 | -.32 | .44 | (1.00) | .44 | -.32 | -.41 | -.17 |
| -.17 | -.41 | -.32 | .44 | (1.00) | .44 | -.32 | -.41 | -.17 |
| -.17 | -.41 | -.32 | .44 | (1.00) | .44 | -.32 | -.41 | -.17 |
| -.17 | -.41 | -.32 | .44 | (1.00) | .44 | -.32 | -.41 | -.17 |
| -.17 | -.41 | -.32 | .44 | (1.00) | .44 | -.32 | -.41 | -.17 |
| -.17 | -.41 | -.32 | .44 | (1.00) | .44 | -.32 | -.41 | -.17 |
| -.17 | -.41 | -.32 | .44 | (1.00) | .44 | -.32 | -.41 | -.17 |

FIG. 4b

| -.03 | -.12 | -.32 | -.44 | -.02 | .77 | (.93) | .22 | -.38 |
|---|---|---|---|---|---|---|---|---|
| -.05 | -.19 | -.41 | -.35 | .31 | (.97) | .70 | -.10 | -.45 |
| -.09 | -.28 | -.45 | -.14 | .65 | (.98) | .37 | -.32 | -.42 |
| -.16 | -.38 | -.40 | .17 | (.90) | .82 | .03 | -.43 | -.34 |
| -.24 | -.44 | -.24 | .51 | (1.00) | .51 | -.24 | -.44 | -.24 |
| -.34 | -.43 | .03 | .82 | (.90) | .17 | -.40 | -.38 | -.16 |
| -.42 | -.32 | .37 | (.98) | .65 | -.14 | -.45 | -.28 | -.09 |
| -.45 | -.10 | .70 | (.97) | .31 | -.35 | -.41 | -.19 | -.05 |
| -.38 | .22 | (.93) | .77 | -.02 | -.44 | -.32 | -.12 | -.03 |

FIG. 4c

| −.01 | −.04 | −.13 | −.28 | −.43 | −.37 | .07 | .70 | (1.00) |
|---|---|---|---|---|---|---|---|---|
| −.04 | −.13 | −.28 | −.43 | −.37 | .07 | .70 | (1.00) | .70 |
| −.13 | −.28 | −.43 | −.37 | .07 | .70 | (1.00) | .70 | .07 |
| −.28 | −.43 | −.37 | .07 | .70 | (1.00) | .70 | .07 | −.37 |
| −.43 | −.37 | .07 | .70 | (1.00) | .70 | .07 | −.37 | −.43 |
| −.37 | .07 | .70 | (1.00) | .70 | .07 | −.37 | −.43 | −.28 |
| .07 | .70 | (1.00) | .70 | .07 | −.37 | −.43 | −.28 | −.13 |
| .70 | (1.00) | .70 | .07 | −.37 | −.43 | −.28 | −.13 | −.04 |
| (1.00) | .70 | .07 | −.37 | −.43 | −.28 | −.13 | −.04 | −.01 |

FIG. 4d

| −.03 | −.05 | −.09 | −.16 | −.24 | −.34 | −.42 | −.45 | −.38 |
|---|---|---|---|---|---|---|---|---|
| −.12 | −.19 | −.28 | −.38 | −.44 | −.43 | −.32 | −.10 | .22 |
| −.32 | −.41 | −.45 | −.40 | −.24 | .03 | .37 | .70 | (.93) |
| −.44 | −.35 | −.14 | .17 | .51 | .82 | (.98) | (.97) | .77 |
| −.02 | .31 | .65 | (.90) | (1.00) | (.90) | .65 | .31 | −.02 |
| .77 | (.97) | (.98) | .82 | .51 | .17 | −.14 | −.35 | −.44 |
| (.93) | .70 | .37 | .03 | −.24 | −.40 | −.45 | −.41 | −.32 |
| .22 | −.10 | −.32 | −.43 | −.44 | −.38 | −.28 | −.19 | −.12 |
| −.38 | −.45 | −.42 | −.34 | −.24 | −.16 | −.09 | −.05 | −.03 |

FIG. 4e

| -.17 | -.17 | -.17 | -.17 | -.17 | -.17 | -.17 | -.17 | -.17 |
|------|------|------|------|------|------|------|------|------|
| -.41 | -.41 | -.41 | -.41 | -.41 | -.41 | -.41 | -.41 | -.41 |
| -.32 | -.32 | -.32 | -.32 | -.32 | -.32 | -.32 | -.32 | -.32 |
| .44  | .44  | .44  | .44  | .44  | .44  | .44  | .44  | .44  |
| (1.00) | (1.00) | (1.00) | (1.00) | (1.00) | (1.00) | (1.00) | (1.00) | (1.00) |
| .44  | .44  | .44  | .44  | .44  | .44  | .44  | .44  | .44  |
| -.32 | -.32 | -.32 | -.32 | -.32 | -.32 | -.32 | -.32 | -.32 |
| -.41 | -.41 | -.41 | -.41 | -.41 | -.41 | -.41 | -.41 | -.41 |
| -.17 | -.17 | -.17 | -.17 | -.17 | -.17 | -.17 | -.17 | -.17 |

FIG. 4f

| -.38 | -.45 | -.42 | -.34 | -.24 | -.16 | -.09 | -.05 | -.03 |
|------|------|------|------|------|------|------|------|------|
| .22  | -.10 | -.32 | -.43 | -.44 | -.38 | -.28 | -.19 | -.12 |
| (.93) | .70  | .37  | .03  | -.24 | -.40 | -.45 | -.41 | -.32 |
| .77  | (.97) | (.98) | .82  | .51  | .17  | -.14 | -.35 | -.44 |
| -.02 | .31  | .65  | (.90) | (1.00) | (.90) | .65  | .31  | -.02 |
| -.44 | -.35 | -.14 | .17  | .51  | .82  | (.98) | (.97) | .77  |
| -.32 | -.41 | -.45 | -.40 | -.24 | .03  | .37  | .70  | (.93) |
| -.12 | -.19 | -.28 | -.38 | -.44 | -.43 | -.32 | -.10 | .22  |
| -.03 | -.05 | -.09 | -.16 | -.24 | -.34 | -.42 | -.45 | -.38 |

FIG. 4g

| 1.00 | .70 | .07 | -.37 | -.43 | -.28 | -.13 | -.04 | -.01 |
|---|---|---|---|---|---|---|---|---|
| .70 | 1.00 | .70 | .07 | -.37 | -.43 | -.28 | -.13 | -.04 |
| .07 | .70 | 1.00 | .70 | .07 | -.37 | -.43 | -.28 | -.13 |
| -.37 | .07 | .70 | 1.00 | .70 | .07 | -.37 | -.43 | -.28 |
| -.43 | -.37 | .07 | .70 | 1.00 | .70 | .07 | -.37 | -.43 |
| -.28 | -.43 | -.37 | .07 | .70 | 1.00 | .70 | .07 | -.37 |
| -.13 | -.28 | -.43 | -.37 | .07 | .70 | 1.00 | .70 | .07 |
| -.04 | -.13 | -.28 | -.43 | -.37 | .07 | .70 | 1.00 | .70 |
| -.01 | -.04 | -.13 | -.28 | -.43 | -.37 | .07 | .70 | 1.00 |

FIG. 4h

| -.38 | .22 | .93 | .77 | -.02 | -.44 | -.32 | -.12 | -.03 |
|---|---|---|---|---|---|---|---|---|
| -.45 | -.10 | .70 | .97 | .31 | -.35 | -.41 | -.19 | -.05 |
| -.42 | -.32 | .37 | .98 | .65 | -.14 | -.45 | -.28 | -.09 |
| -.34 | -.43 | .03 | .82 | .90 | .17 | -.40 | -.38 | -.16 |
| -.24 | -.44 | -.24 | .51 | 1.00 | .51 | -.24 | -.44 | -.24 |
| -.16 | -.38 | -.40 | .17 | .90 | .82 | .03 | -.43 | -.34 |
| -.09 | -.28 | -.45 | -.14 | .65 | .98 | .37 | -.32 | -.42 |
| -.05 | -.19 | -.41 | -.35 | .31 | .97 | .70 | -.10 | -.45 |
| -.03 | -.12 | -.32 | -.44 | -.02 | .77 | .93 | .22 | -.38 |

METHOD FOR AUTOMATICALLY LOCATING IMAGE PATTERN IN DIGITAL IMAGES

FIELD OF THE INVENTION

This invention relates in general to a method for automatically locating instances of a target image pattern in a digital image, and more particularly relates to a method for automatically locating intervertebral disks in lumbar spine for computed radiography produced digital radiographic images.

BACKGROUND OF THE INVENTION

Computed radiography is a technique in which a latent radiographic image formed in a reusable storage phosphor is read out to produce a digital radiographic image.

Images acquired by computed radiography (CR) require a tone scale mapping for a diagnostically satisfactory visual examination. The tone scale is the mapping between the input code values and the output code values for display media, such as film density of a photographic film or luminance of a cathode-ray-tube monitor. Prior to the determination of the tone scale curve, the desired region of interest in a CR image (that is, the body parts) should be separated from the irrelevant objects (for example, the background and foreground) via a segmentation algorithm. For a low signal to noise ratio image, the segmentation task is particularly difficult. Hence, for some body parts and projections, the tone scale algorithm does not give the desired contrast look of the images. Lateral lumbar spine CR images are one of these types of image.

Various methods for locating/identifying the bone region of interest have been proposed. For example, in order to use a posterior/anterior (PA) chest radiograph to analyze lung texture, the inter-rib bones shown in the PA chest image need to be removed. U.S. Pat. No. 4,851,984, issued Jul. 25, 1989, to inventors K. Doi, et al. teaches a method to locate inter-rib spaces in digital chest radiograph images. First, a lung field is defined by determining the rib cage edge boundary. A horizontal signal profile is obtained at a predetermined vertical location. The pixel location at which the second derivative of this horizontal profile is minimum is defined as the rib cage edge boundary. Then two vertical profiles in the periphery of both lungs are fitted with a shift-invariant sinusoidal function. This technique assumes that the horizontal line is always perpendicular to the spinal column. Moreover, it assumes that the relative vertical locations of the objects are known a priori. Therefore, U.S. Pat. No. 4,851,984 does not teach a fully automatic method for locating instances of an image pattern. Furthermore, the lumbar spine bone structure is different from the inter-rib bone structure. The profiles with sinusoidal function do not fit the lumbar spine bone. U.S. Pat. No. 5,268,967, issued December, 1993, to inventors B. K. Jang, et al. teaches a method of using edge density for segmenting image into foreground, background, and body parts regions. Yet, the lumbar spine image needs further segmentation of lumbar spine bone region from soft tissue inside the body part. Because the lumbar spine region which is even separated from the background and the foreground still spans a large dynamic range, that is, a wide code value range. This causes low contrast look in an output display.

Histogram methods have been used to locate the bone region of interest. U.S. Pat. No. 5,228,068, issued Jul. 13, 1993, to inventor R. B. Mazess, teaches a method to determine and analyze vertebral morphology by evaluating the approximate center location of each vertebra from a digital lateral vertebral scan. The centers are located by evaluating the horizontal and vertical histograms. The horizontal histogram is constructed along a line cross each anterior-posterior border of the vertebra. The vertical histogram is obtained along a line cross superior-inferior border, which directs the spine column. Because the patient is supported in the supine position on a table so that the vertebrae of the spine are generally aligned with the scan direction. However, because of the curvature of the spine, the angle of the vertebrae, that is, the angle of an anterior border, a posterior border, a superior border, and an inferior border with respect to the scan direction will vary among vertebrae. This method requires that this variation be accommodated by the trained eye of a physician in estimating the initial positions of lines which horizontal and vertical histogram are generated from. The rigid assumption about the relative orientation of the image relative to the body makes the invention sensitive to orientation error and can not be used in automatic mode for general image orientations.

Another histogram-based method disclosed in U.S. Pat. No. 4,951,201 is used to determine the image body posture. In order to produce a better view of digital radiography, it is important to know if the object is imaged from its front side or lateral side. For example, for a chest image, the imaged thoracic vertebrae is of a relatively low density when it is imaged from its front side, and of relatively high density when it is imaged from its lateral side. This method determines imaged body posture by analyzing the histogram characteristics along a prescribed direction across the image. However, the method does not describe whether a prescribed direction is determined by a user interaction or by an automatic algorithm.

Other methods have used shape information to locate the bone region of interest. U.S. Pat. No. 4,922,915, issued May 8, 1990, to inventor B. A. Arnold, teaches a method to place an region of interest (ROI) of regular (e.g., elliptical) or irregular shape in a specific region of the image of the patient's anatomy, such as the trabecular bone region of the patient's spine. The cross-section image of an upper region of vertebra body contains the cortical bone image which appears as an outer ring, the trabecular bone image which occupies a portion of inside the ring, and the basivertebral vein image which occupies another small portion inside the ring. It is desired to exclude the basivertebrae vein from the trabecular bone image. This method requires that the operator positions the enlarged region of interest so that it encompasses the top region of the vertebral body including the trabecular bone image but excluding the basivertebral vein image. Then the template search and histogram analysis algorithm are used to place the trabecular bone region.

Some researchers have proposed methods to segment images of the hand bone for the purpose of age assessment (D. T. Morris et al., "Segmentation of the finger bones as a prerequisite for the determination of bone age," *Image and Vision Computing*, Vol. 12, No. 4, pp. 239–246, May 1994; E. Pietka et al., "Feature extraction in carpal-bone analysis," *IEEE Transactions on Medical Imaging*, Vol. 12, No. 1, pp. 44–49, 1994; E. Pietka et al., "Computer-assisted phalangeal analysis in skeletal age assessment," *IEEE Transactions on Medical Imaging*, Vol. 10, No. 4, pp. 616–619, December 1991; C.-L. Chang et al., "Computer-aided diagnosis: detection and characterization of hyperparathyroidism in digital hand radiographs," *Medical Physics*, 20(4), pp. 983–992, July/August 1993.). In the first three publications, the hand bone region of interest was defined using a standard thresholding technique to separate the hand from the background.

Unfortunately, thresholding is not a robust and reliable image segmentation method for the texture-rich CR medical images. In the last publication, the extraction of the hand region of interest was performed manually. Then, an edge filter was applied to extract edges of finger bones. However, an edge filter usually produces numerous false alarms and misses; a complicated post processing is needed to remove these false alarms. This proposed method also relies on the user (manual) supervision which is not desirable.

The lumbar spine bone has a more complicated structure than the hand bone. Simple edge filtering cannot extract lumbar spine bone features (P. P. Smyth et al., "Automatic measurement of vertebral shape using active shape models," *Proceedings of British Machine Vision Conference*, Edinburge, Sep. 9–12, 1996; J. M. Muggleton et al., "Automatic location of vertebrae in digitized videofluoroscopic images of the lumbar spine," *Medical Engineering and Physics*, Vol. 19, No. 1, pp. 77–89, 1997; M. P. Chwialkowski et al., "Automated localization and identification of lower spinal anatomy in Magnetic Resonance images," *Computers and Biomedical Research*, 24(2), pp. 99–117, 1991; G. Taascini et al., "Automatic quantitative analysis of lumbar bone-radiographs," *Proceedings of the 1993 IEEE Nuclear Science Symposium & Medical Imaging Conference*, Vol. 3, pp. 1722–1726, San Francisco, Calif., Oct. 30–Nov. 6, 1993). Various methods have been proposed to locate the lumbar spine bone, for example, active shape models (Smyth et al.), template based cross-correlation matching (Muggleton et al.), and a combination of morphological methods and pattern analysis (Chwialkowski et al; Taascini et al.). However, all these methods require manually selecting the lumbar bone region of interest. In Smyth et al., the operator was asked to select three initialization points: one point at the top of vertebra T7 (number 7 vertebra of thoracic spine), one at the top of T12 (number 12 vertebra of thoracic spine), and one at the bottom of L4 (number 4 vertebra of lumbar spine). In Muggleton et al., each of the vertebrae in the first frame was identified manually by marking the four body (vertebra) corners as reference points for describing/identifying the vertebral position in each subsequent frame. In Chwialkowski et al., three radiologists examined a series of images and identified the center image, which were used as vertebra template. In Taascini et al., the human operator initialized the process by circumscribing L1 vertebra inside a rectangle selected with a mouse pointer device.

SUMMARY OF THE INVENTION

The present invention provides a solution to these problems. According to a feature of the present invention, there is provided a method for automatically locating instances of a target pattern in digital images, comprising the steps of: providing a digital image; detecting a first simple feature associated with the target patterns in the digital image; for each detected feature, searching, in its spatial neighborhood, a second or a plural of other features associated with the target patterns; for each pair of plural of features detected, checking the consistency of image intensity profile with the target pattern within the spatial neighborhood as delimited by the feature points detected in the searching and detecting steps; and labeling those image regions that are found to be consistent with the structure of the target pattern in the checking step.

ADVANTAGEOUS EFFECT OF THE INVENTION

The invention has the following advantages.
1. Optimal tone scale adjustment of a target image pattern in a digital image is facilitated. By locating lumbar spine in a computed radiographic image optimal tone scale adjustment for a diagnostically satisfactory visual examination is facilitated.
2. Image segmentation and bone morphology analysis in a radiographic digital image is facilitated.

BRIEF DESCRIPTION OF THE DRAWINGS

FIG. 1($b$) is a block diagram showing the method of the present invention as applied to the problem of automatically locating the lumbar bone pattern from lateral lumbar spine (LAT Lspine) computed radiographs.

FIG. 2($b$) is a graphical view showing the image profile of one line in a full resolution Lspine image. The profile shows 3 ridge-valley shaped curves corresponding to 3 intervertebral disk spaces.

FIGS. 4($a$)–4($h$) are diagram views showing the directional filter coefficients. 4($a$)θ=0; 4($b$)θ=π/8; 4($c$)θ=π/4; 4($d$)θ=⅜π; 4($e$)θ=π; 4($f$)θ=⅝π; 4($g$)θ=¾π; 4($h$)θ=⅞π.

FIG. 10($b$) is a graphical view showing the image profile of a horizontal line of one Lspine image processed by the image pattern tone scale of the present invention.

DETAILED DESCRIPTION OF THE INVENTION

The present invention discloses a general method for automatically locating instances of a target image pattern in a digital image. In particular, it discloses a method for automatically locating the lumbar bone pattern from lateral lumbar spine (LAT Lspine) computed radiographs. The bone pattern in Lspine images was studied and it was found that the intervertebral disk spaces between Lspine vertebrae were prominent features. The fringes of Lspine disk spaces appear to be ridges instead of edges. The image profile of the intervertebral disk space presents a ridge-valley shaped curve. The valley represents the less dense portion of the intervertebral disk space. The two ridges represent two fringes of the disk space, which are superior and inferior vertebral endplates, respectively. Hence, a directional ridge filter is designed to extract the Lspine disk space ridge points. The image profile shape condition is used to constrain the selection of a pair of disk space ridge points.

All the points on the lines connecting pairs of disk space ridges form a histogram, called the image pattern histogram. This histogram distribution represents the code value distribution of the Lspine bone region of interest. The use of the constraint of the image profile shape minimizes the contribution of non-bone patterns in the image pattern histogram. By analyzing this histogram, the dynamic range of Lspine image can be narrowed down to the sub-region which is the most important body part to be examined, that is the Lspine bone pattern. The corresponding digital image code value range corresponding to the intervertebral disk spaces is then input to the visually optimized tone scale algorithm to generate the desired mapping to obtain a diagnostically satisfactory rendering of the image.

Since the ridge filter is simple and is easy to implement, the present invention provides an efficient means for locating the Lspine disk space ridge points and constructing the image pattern histogram. The image pattern locating algorithm is also easy to extend to other targets in digital radiography images, such as cylindrical bones.

In the following description, the method of the invention will be described in locating Lspine bone pattern and Lspine intervertebral disk spaces.

Figure 12:
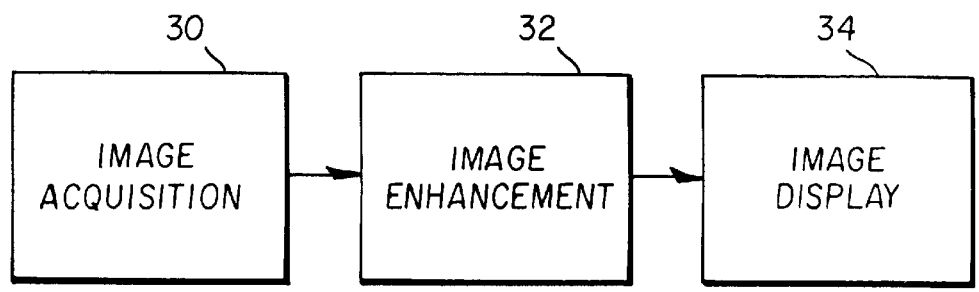
FIG. 12 is a block diagram of a digital image system incorporating the present invention.

The digital image is acquired by image acquisition system 30 (FIG. 12). The digital image is processed by image enhancement system 32 and the processed image is output to image display 34. Image acquisition system 30 can be one of the following: a computed radiography system; radiographic film digitizer; diagnostic image modality (CT, MRI, US, NM, PET); digital image archive. The image display can be a soft copy display (CRT, liquid crystal display) or a hard copy (film, paper).

Figure 11:
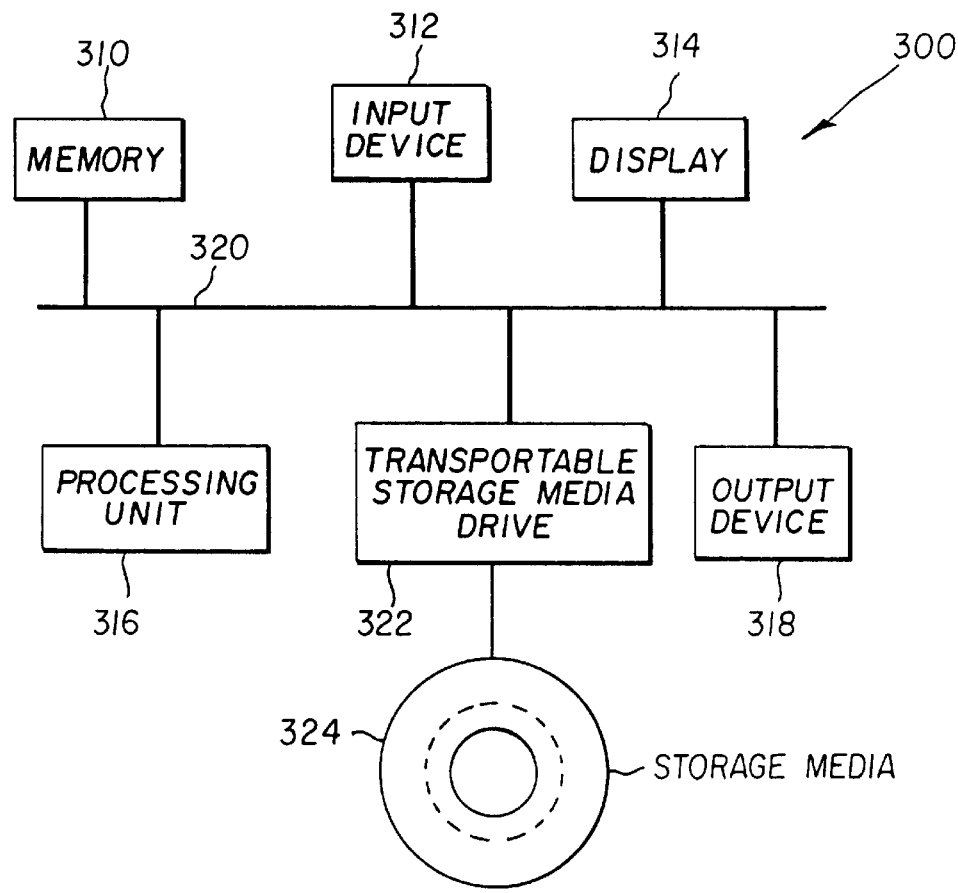
FIG. 11 is a block diagram of a digital image processing system for carrying out the present invention.

The digital image is processed in image enhancement system 32 (FIG. 12) according to the method of the present invention. System 32 can take the form of a digital computer, such as illustrated in FIG. 11. In such case, one or more of the steps of said method can be carried out using software routines. Image processor can also include hardware or firmware for carrying out one or more of the method steps. Thus, the steps of the method of the invention can be carried out using software, firmware, and hardware, either alone or in any preferable combination.

As shown in FIG. 11, a digital computer 300 includes a memory 310 for storing digital images, application programs, operating system, etc. Memory 310 can include mass memory (such as a hard magnetic disc or CD ROM), and fast memory (such as RAM). Computer 300 also includes input device 312 (such as a keyboard, mouse, touch screen), display 314 (CRT monitor, LCD), central processing unit 316 (microprocessor), output device 318 (thermal printer, dot matrix printer, laser printer, ink jet printer). Components 310, 312, 314,316, 318 are connected together by control/data bus 320. Computer 300 can include a transportable storage medium drive 322 for reading from and/or writing to transportable storage media 324, such as a floppy magnetic disk or writeable optical compact disk (CD).

As used in this application, computer readable storage medium can include, specifically, memory 310 and transportable storage medium 324. More generally, computer storage medium may comprise, for example, magnetic storage media, such as magnetic disk (hard drive, floppy disk) or magnetic tape; optical storage media, such as optical disk, optical tape, or machine readable bar code; solid state electronic storage devices, such as random access memory (RAM), read only memory (ROM); or any other physical device or medium which can be employed to store a computer program.

Following is the method of the invention as applied to finding Lspine bone pattern and the major steps of locating Lspine intervertebral disk spaces.

Figure 1A:
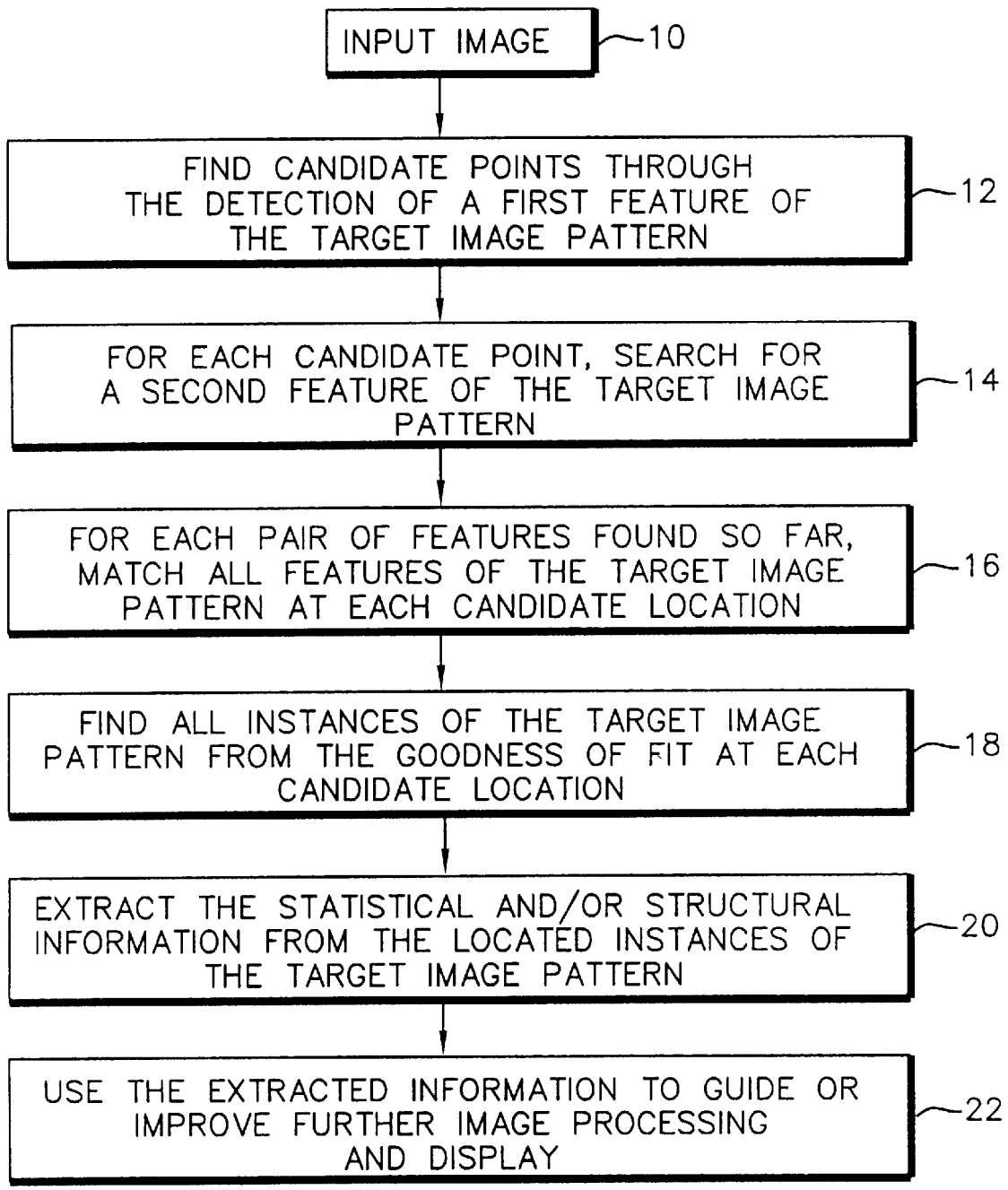
FIG. 1($a$) is a block diagram showing the general method of the present invention for automatically locating instances of a target image pattern in a digital image.

Referring now to FIG. 1a, there is shown a flow diagram of the general method of the present invention for automatically locating instances of a target image pattern in a digital image. A digital image is input (box 10). Then, find candidate points through the detection of a first feature of the target image pattern (box 12). For each candidate point, search for a second feature of the target image pattern (box 14). For each pair of features found so far, match all features of the target image pattern at each candidate location (box 16). Next, find all instances of the target image pattern from the goodness of fit at each candidate location (box 18). Then, extract the statistical and/or structural information from the located instances of the target image pattern (box 20). Lastly, use the extracted information to guide or improve further image processing and display (box 22).

Figure 1B:
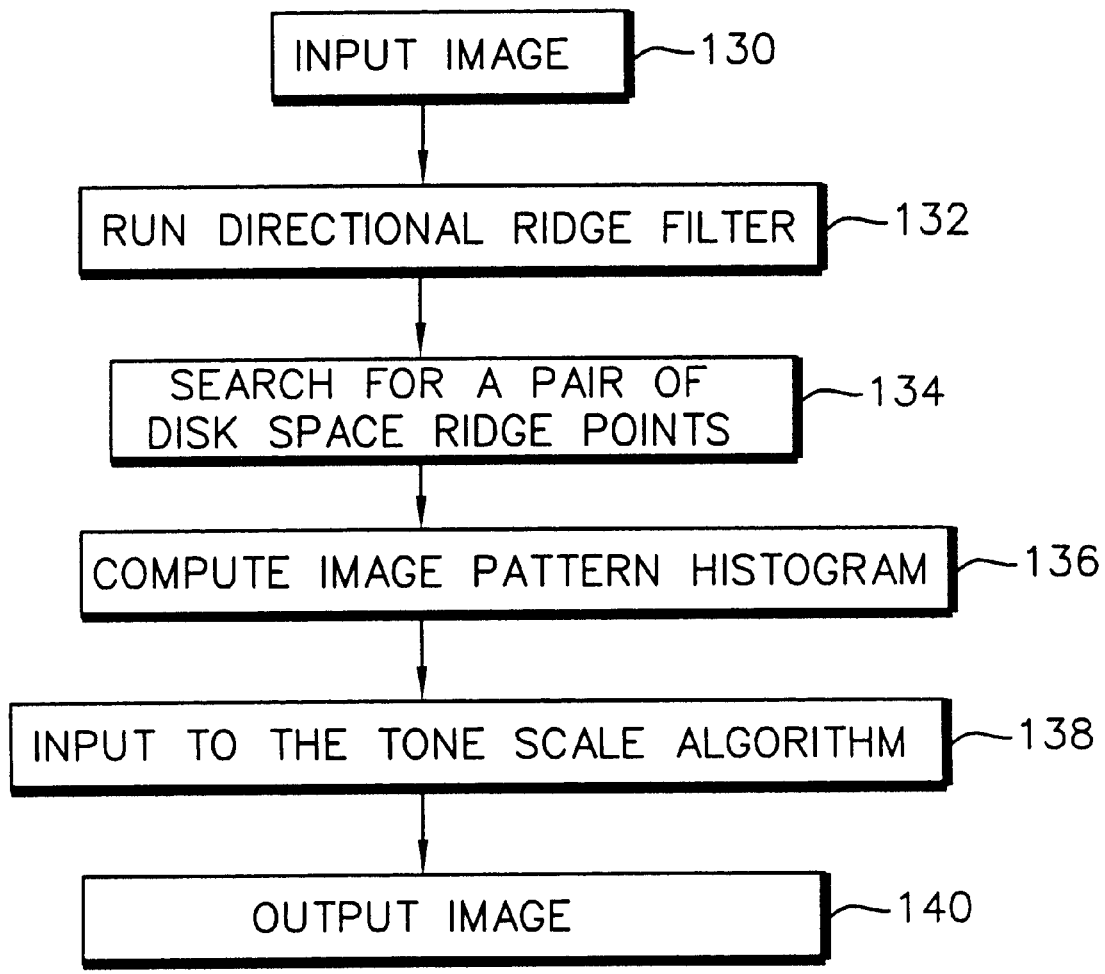

FIG. 1b is a flow diagram of the method of the present invention as applied to the problem of automatically locating the lumbar bone pattern from lateral lumbar spin (LAT Lspine) computed radiographs. A digital image having a lateral lumbar spine is provided (box 130). A directional ridge filter is run on the digital image (box 132). Then, search for pairs of disk space ridge points (box 134). An image pattern histogram is computed from the found pairs of disk space ridge points (box 136). Next, a tone scale curve of the provided digital image is constructed from the image pattern histogram (box 138). Lastly, the tone scale curve is applied to the provided digital image to produce an output image (box 140).

Lspine Bone Pattern

Figure 2A:
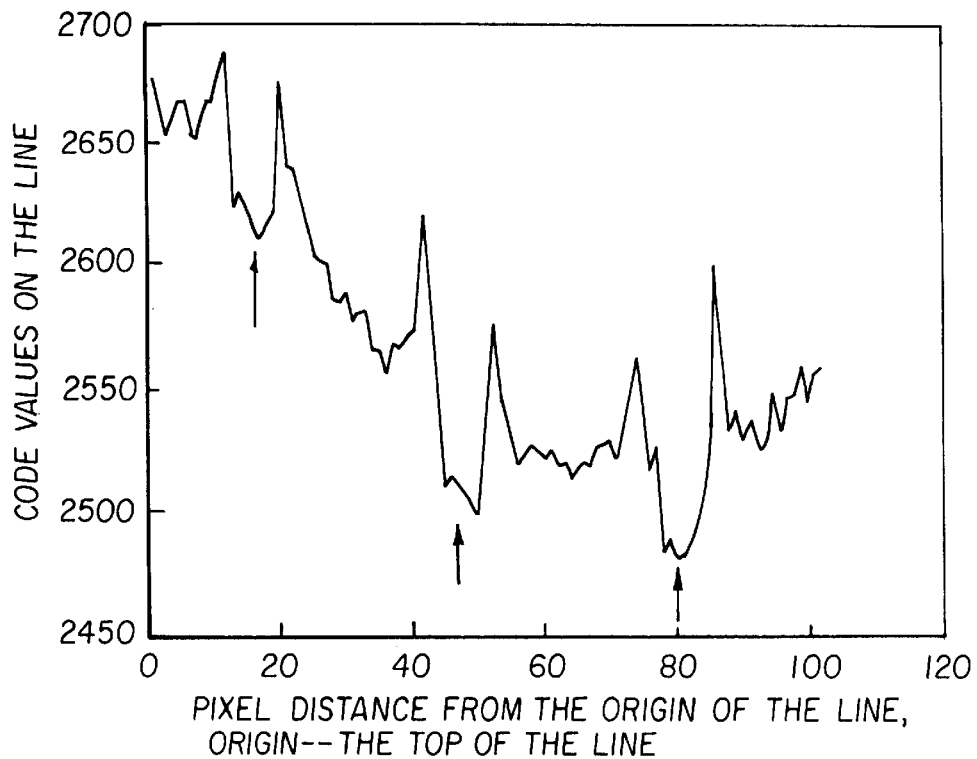
FIG. 2($a$) is a graphical view showing the image profile of one line in a sub-sampled Lspine image. The profile shows 3 ridge-valley shaped curves corresponding to 3 intervertebral disk spaces.

An Lspine image contains several vertebrae and intervertebral disk spaces. A line is analyzed which crosses 4 vertebrae and 3 intervertebral disk spaces. Its image profile (the code-values on that line) is shown in FIG. 2(a). From the image profile, we observe that there are 3 ridge-valley shaped curves corresponding to 3 intervertebral disk spaces. These 3 ridge-valley shaped curves are located at the distance 15, 45 and 80, respectively in FIG. 2(a). The valley represents the less dense portion of the intervertebral disk space. The two ridges represent two fringes of the disk space, which are superior vertebral endplate and inferior vertebral endplate, respectively. The reason we call these curves as ridge-valley shapes is that they do not have the step-edge shape.

In normal x-ray image viewing, the bones usually appear white. In order to display the Lspine image in reflectance (on the paper) with white bone appearance, the image polarity needs to be reversed. The CR digital image is stored at 12 bits per pixel (0-4095 code value—CV). Therefore, the image polarity is reversed by using 4095—code values. The image profile (code values) shown in FIG. 2(a) is the reversed image polarity. In this way, the higher code values represent the brighter area; and the lower code values represent the darker area. This is opposite as in the film viewing, which is, the lower code values (corresponding lower x-ray log exposures) represent the brighter area, and vice versa.

Figure 2B:
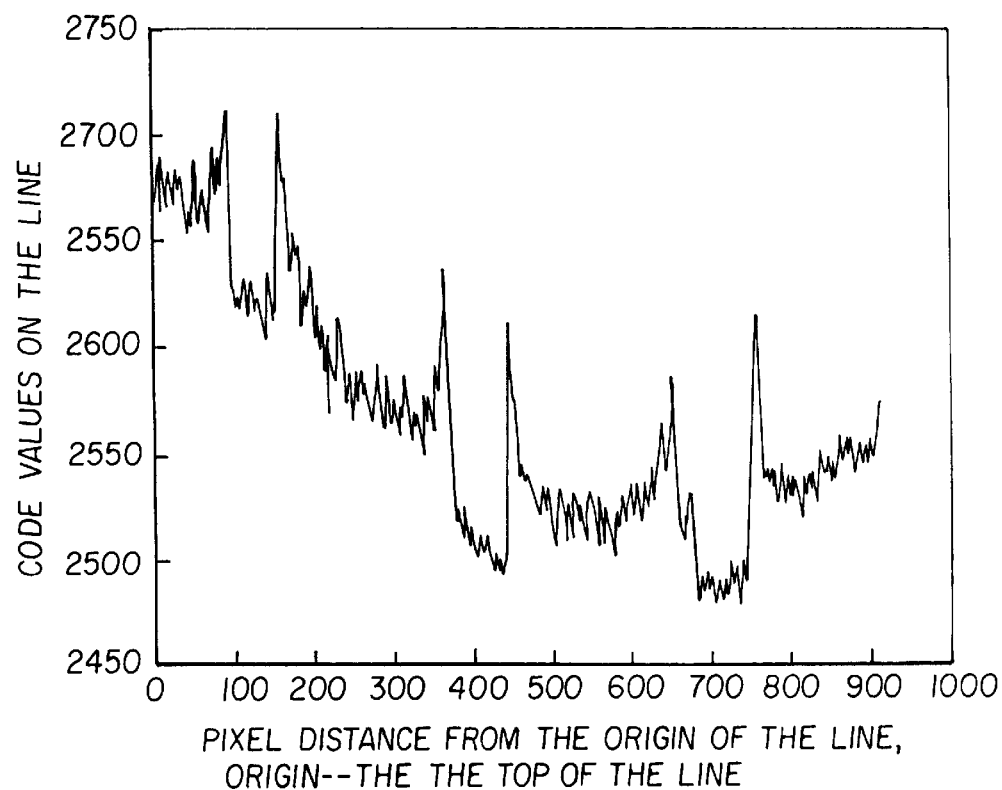

The size of the image which is acquired by the CR system is about 2500 lines×2000 pixels per line. The image profile shown in FIG. 2(a) is obtained from a sub-sampled version of the original CR system image; the size of the sub-sampled image is about 277×227 pixels (9:1 sub-sample ratio). The locating of the Lspine bone pattern is performed on the sub-sampled images. Since these are low resolution images, it is wished to determine whether the sub-sampling has adverse effects in the Lspine bone feature representation. Therefore, there is analyzed the same line mentioned above which crosses 4 vertebrae and 3 intervertebral disk spaces in the full resolution image. FIG. 2(b) shows the resultant image profile. From the image profile of the full resolution image, it can be seen that the valley has a relatively flat bottom and it does not have a distinguishable shape. However, the ridge has a sharp-pointed shape. The same phenomenon was observed in the image profile of the sub-sampled image in FIG. 2(a). Hence, the Lspine bone pattern shown in the low resolution image (FIG. 2(a)) contains reliable information base for Lspine locating.

Hence, the intervertebral disk space and its image profile are selected to represent the Lspine image pattern. A filter to extract the ridge shape intervertebral disk space pattern is described in the following section.

Locating Lspine Intervertebral Disk Spaces
(1) Horizontal Ridge Filtering

Figure 3:
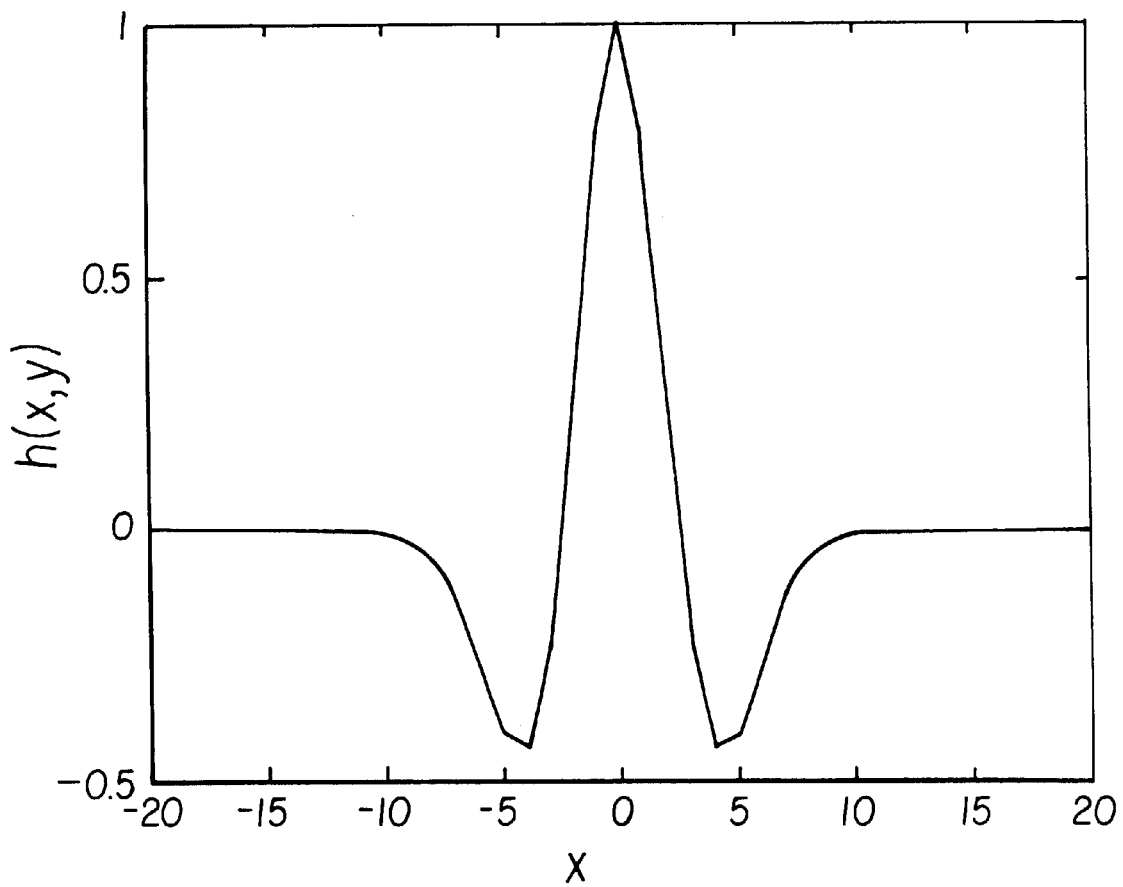
FIG. 3 is a graphical view showing the horizontal ridge filter—the second derivative of the Gaussian function, $$h(x, y) = \left(1 - \frac{x^2}{\sigma_x^2}\right) e^{-\frac{x^2}{2\sigma_x^2}}, \quad \sigma_x = 2.5$$

Since Lspine intervertebral disk spaces represented in the image profile behave as ridges rather than edges, we need to design a filter that can extract these ridges. Among the popular filters, the second derivative of the Gaussian function has the shape of a ridge, as shown in FIG. 3. The ridge filter is designed for 2D images. For a horizontal ridge, it is the second derivative of the Gaussian function in x-direction (the horizontal direction) and a constant in y-direction (the vertical direction), that is, $$h(x, y) = \left(1 - \frac{x^2}{\sigma_x^2}\right) e^{-\frac{x^2}{2\sigma_x^2}}$$

where $\sigma_x$ is the standard deviation of the Gaussian function.
(2) Directional Ridge Filtering For a given Lspine image, the disk space ridges could be in any direction based on how the patient was positioned when the Lspine image was captured. However, the highest response of the ridge filter corresponds to the direction orthogonal to the ridges of the disk spaces. It can be seen that the response of the ridge filter diminishes as one turns away from this direction, until it vanishes at right angles to it. To determine the ridge angular direction, the above horizontal ridge filter is rotated with increments of $\pi/8$, that is, the following 8 angular directions:

$$\theta = 0, \frac{\pi}{8}, \frac{\pi}{4}, \frac{3}{8}\pi, \frac{\pi}{2}, \frac{5}{8}\pi, \frac{3}{4}\pi, \frac{7}{8}\pi$$

FIGS. 4 (a)–(h) show the directional filter in grey level at the above 8 directions. Then, each of these 8 directional ridge filters, call them $h_k(m,n)$, k=1, . . . , 8, is convolved with the Lspine image, i(m,n). The response of the k-th filter, k=1, . . . , 8, is obtained by the following, $$r_k(m,n) = h_k(m,n) ** i(m,n).$$

Figure 5:
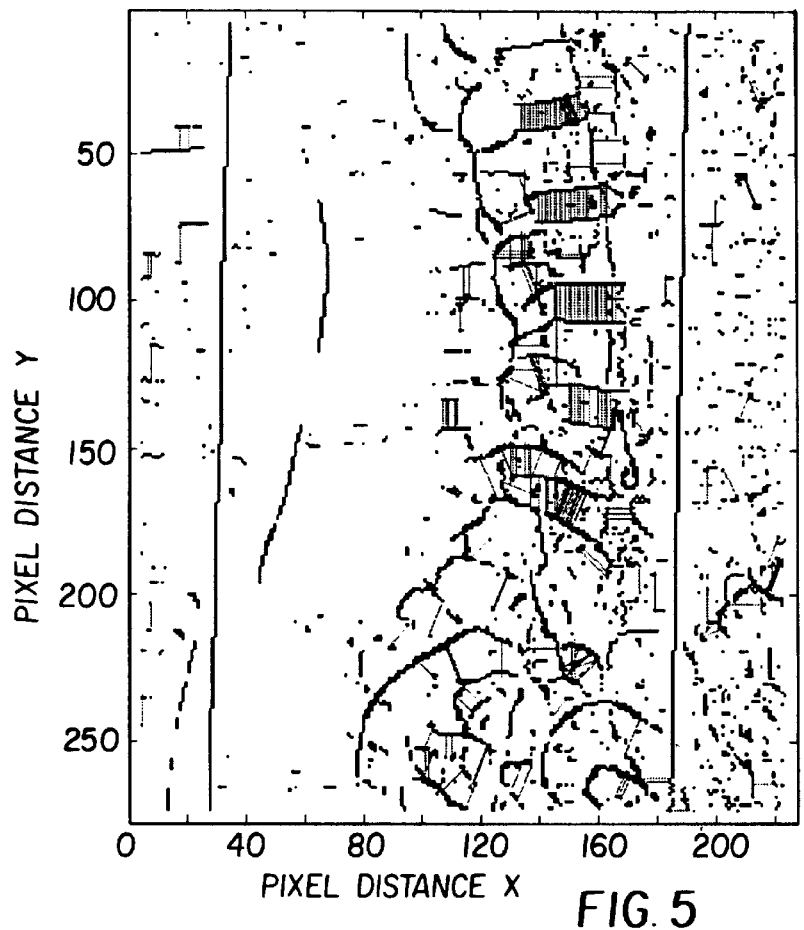
FIG. 5 is a diagrammatic view showing the ridge points obtained by the directional ridge filter for one Lspine image.

The final ridge response at an image point is obtained as the maximum response of the ridge filter among these 8 directions, that is, $$\text{ridge}(m,n) = \max\{r_k(m,n); k=1, 2, \ldots, 8\}$$

where, $r_k(m,n)$ is the response of the ridge filter in the k-th direction at the pixel location (m,n). A ridge point is defined as a pixel that has the local maximum ridge response perpendicular to its ridge direction. FIG. 5 shows the ridge points of a Lspine image.
(3) Determining Ridge Filter Parameters The parameters to be determined for the ridge filter are the window size and the standard deviation $\sigma_x$. These parameters can be determined by the physical pixel spacing size in centimeters. For CR images, there are three types of pixel spacing based on the techniques and the plate sizes which are used to capture the image. They are a) 97 microns/pixel, (0.097 mm/pixel), 8×10 inches image plate;

b) 115 microns/pixel, (0.115 mm/pixel), 11×14 inches image plate;

c) 171 microns/pixel, (0.171 mm/pixel), 14×17 inches image plate.

The header of the CR image contains this information. In the case when no specific information can be found in the header, a default pixel spacing, e.g., 171 microns/pixel is used.

The distance between two ridges of a disk space is in a reasonable range for human being, that is within 2 cm. Then, the window size of the ridge filter is selected to be 1.5 cm such that no more than one disk spaces can be within the window. The selection of the standard deviation $\sigma_x$ is based on the experiment on a number of images. For Lspine image database, $\sigma_x$=0.4 cm is selected. Then, the filter parameters in pixel units for different resolution images can be determined according to the pixel spacing size.

Figure 6:
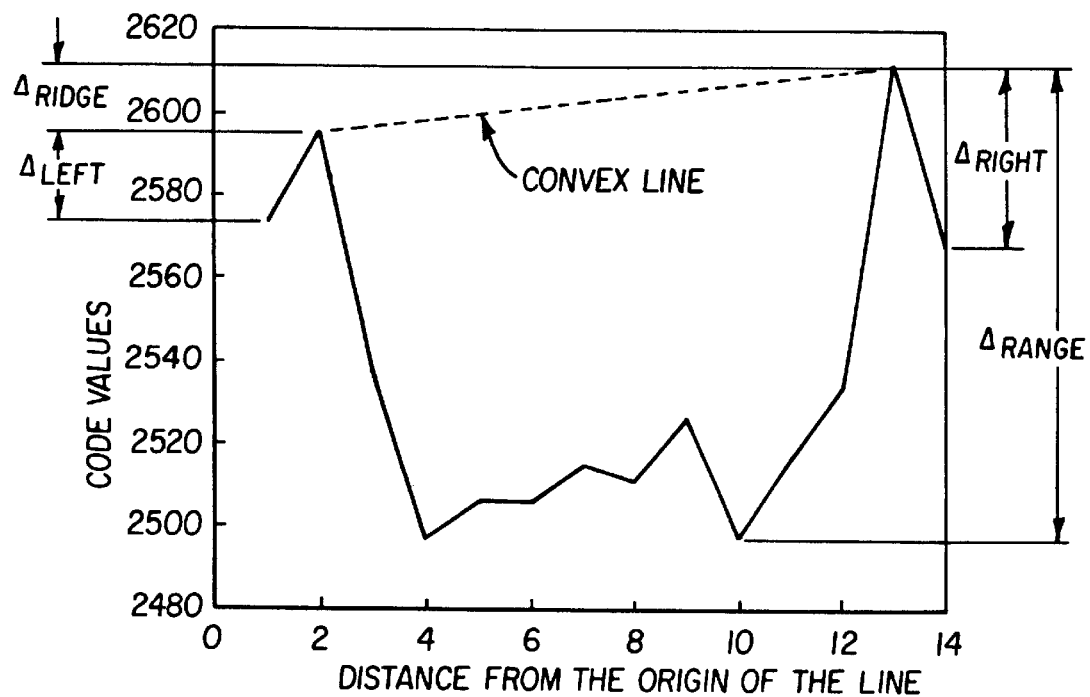
FIG. 6 is a graphical view showing an image profile of a line connecting a pair of disk space ridge points obtained in FIG. 5. The measurements, $\Delta_{left}$, $\Delta_{right}$, $\Delta_{range}$, $\Delta_{ridge}$, and the convex line, are used in the profile shape conditions to search for a pair of disk space ridge points.
Figure 7:
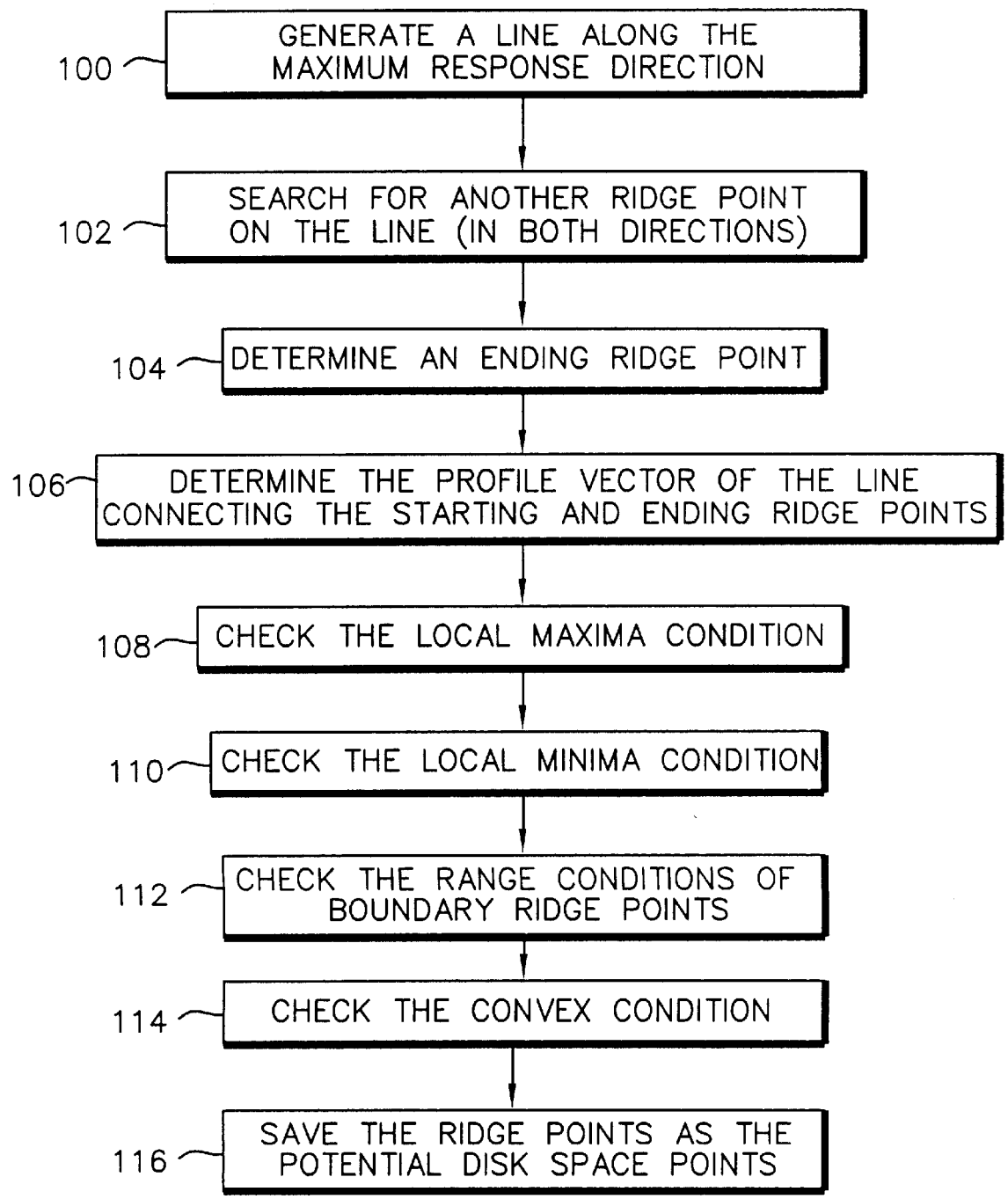
FIG. 7 is a block diagram of a method for searching for a pair of disk space ridge points.

The window size w×w and the standard deviation of the Gaussian function $\sigma_x$ in pixel units for three different resolution images are listed in the following. (Notes: the numbers listed in the following are used for sub-sample-by-9 images.)

a) For images with 97 microns/pixel, w=17, $\sigma_x$=4.58;

b) For images with 115 microns/pixel, w=15, $\sigma_x$=3.86;

c) For images with 171 microns/pixel, w=9, $\sigma_x$=2.59;
(4) Searching for Pair of Disk Space Ridge Points Due to the presence of noise and other image objects, e.g., the collimation mask, etc., in the acquired Lspine image, many other ridge points, in addition to the disk space ridge points, are found in the Lspine image. This can be seen in FIG. 5. Only the disk space ridge points are desirable. It was noticed that the ridges of intervertebral disk spaces form parallel lines, which represent the superior vertebral endplate and inferior vertebral endplate, respectively. A disk space ridge point is always corresponding to another ridge point to form a pair of ridge points. A typical profile of a line which connects a pair of disk space ridge points is shown in FIG. 6. The algorithm to search for a pair of disk space ridge points, including the profile shape conditions, is outlined in the following. FIG. 7 shows a block diagram of this searching algorithm.

1. For each ridge point, generate a line along the direction with the maximum response of the ridge filter (box 100). The length of the line is set to be l=2.2 cm for the Lspine images in our database. The length of this line in pixel units for three different resolution images are:

a) For images with 97 microns/pixel, l=26;
b) For images with 115 microns/pixel, l=22;
c) For images with 171 microns/pixel, l=15;

2. On that line, search for another ridge point (in both directions) (box 102). To reduce the noise effects, the search starts from the middle point of that line away from the starting ridge point.

3. After detecting an "ending" ridge point, determine the absolute difference of the angular directions of the starting and the ending ridge points (box 104). If this absolute difference is less than or equal to $\pi/8$, then accept the ending ridge point.

4. Identify the line that connects the starting and the ending ridge points. Suppose there are n pixel points on this line. Each pixel value on this line is determined by bilinear interpolation. Denote the profile vector for this line to be $CV(1, \ldots, n)$ (box 106).

5. Accept this ending ridge point as a disk space ridge point if the following profile shape conditions are satisfied.

(a) For a valid pair of disk space ridge points, the starting and the ending ridge points should be local maxima of the above profile vector (box 108). That is, $$CV(2) > \max(CV(1), CV(3)), CV(n-1) > \max(CV(n-2), CV(n)).$$

In some cases, it is necessary to add one more point along the above line outside of either the starting or/and the ending ridge point. In this way, it will give a guarantee that the starting and the ending ridge points are the second and the second from the last point on that line, respectively. For the simplicity, let the number of pixel points on this modified line to be n. For example, in FIG. 6, n=14.

(b) For a valid pair of disk space ridge points, the minimum of the profile does not occur at the boundary (ridge points) (box 110). This translates to the following criterion:

$$\min(CV) = CV(m), 2 < m < n-1$$

(c) Let the differential (point to point) change at the boundary ridge points be $$\Delta_{left} = CV(2) - CV(1), \Delta_{right} = CV(n-1) - CV(n)$$

and the code value range of the profile be $$\Delta_{range} = \max(CV) - \min(CV)$$

For a valid pair of disk space ridge points, the maximum of the differential boundary changes should be a fraction of the code value range, that is, $$\max(\Delta_{left}, \Delta_{right}) < \delta_1 \times \Delta_{range},$$

where $0 < \delta_1 < 1$ (box 112). In our experiment, we used $\delta_1 = 0.55$.

(d) Define the differential change between the two ridge points to be $$\Delta_{ridge} = |CV(n-1) - CV(2)|.$$

For a valid pair of disk space ridge points, this differential change should be a fraction of the range of code values. That is, $$\Delta_{ridge} < \delta_2 \times \Delta_{range},$$

where $0 < \delta_2 < 1$. In our experiment, we used $\delta_2 = 0.55$.

(e) For a valid pair of disk space ridge points, the profile should satisfy the convex condition (box 114). That is, the points between the starting and the ending ridge points are below the line that connects the two ridge points on the profile (see the convex line in FIG. 6).

6. If above criteria are satisfied, save the ridge points as the potential disk space points (box 116).

Figure 8:
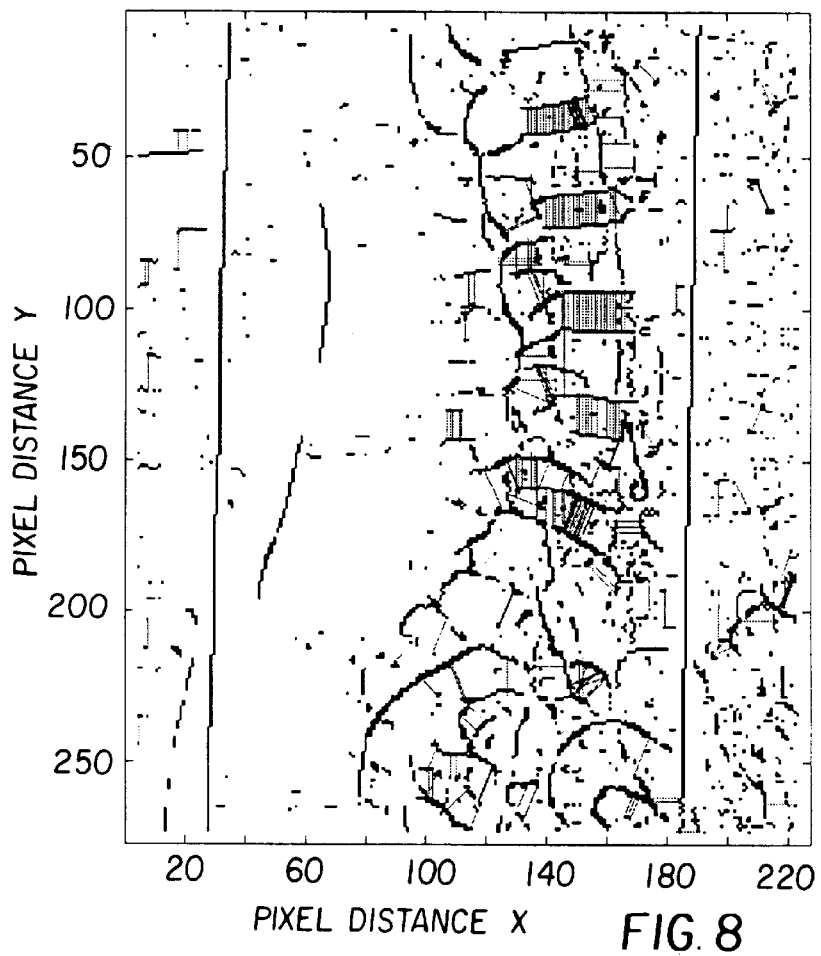
FIG. 8 is a diagrammatic view showing the lines connecting the searched pairs of the disk space ridge points for one Lspine image.

FIG. 8 shows the searched disk space ridge points and the lines that connect the pairs of the ridge points for a Lspine image.

(5) From Lspine Disk Spaces to the Tone Scale Curve

Figure 9:
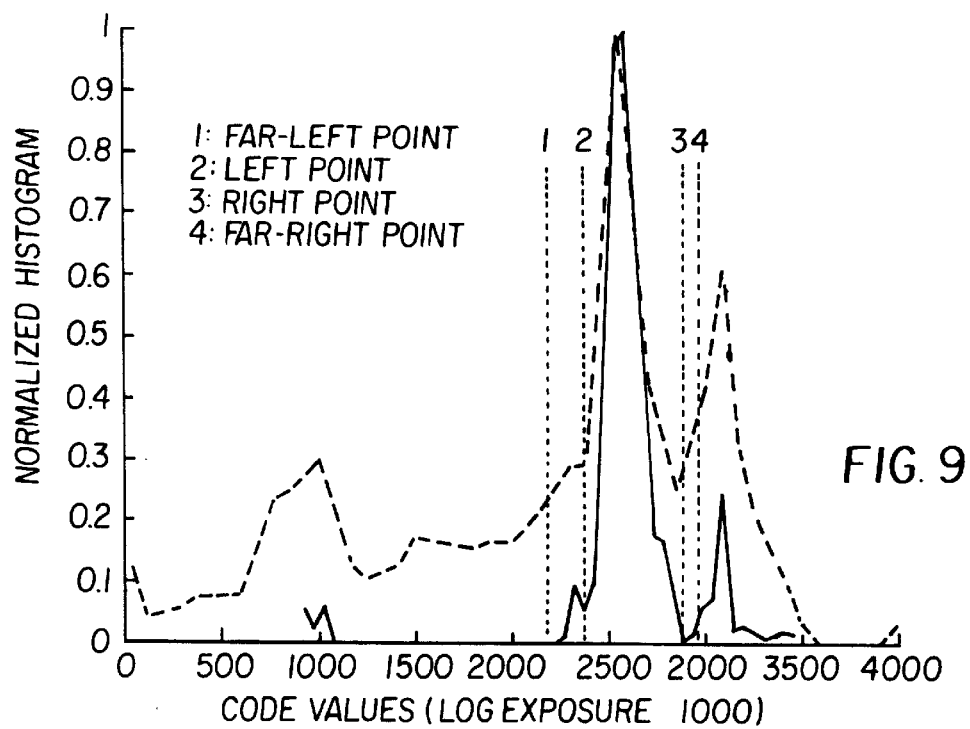
FIG. 9 is a graphical view showing the image structure histogram (obtained by the code values of the lines connecting the searched pairs of the disk space ridge points, the solid line), and the code-value histogram (obtained from the entire Lspine image, the dashed line).

After identifying the valid disk space ridge points, the information of this region of interest is used in constructing the tone scale curve of the Lspine image. For this purpose, we form the histogram of the pixel points which fall on the lines that connect the valid pairs of ridge points. This histogram represents the code value distribution of the disk spaces, which are bone patterns in the Lspine image, called the image pattern histogram. FIG. 9 shows the image pattern histogram (the solid line) and the code-value histogram of the entire image (the dashed line) for a Lspine image. From FIG. 9, we observe that most of code values of the region of interest fall between 2200 to 2900, while the code values of the entire image span the range of 0 to 4000.

From the image pattern histogram, four points in the input Lspine image code value range can be identified, which are essential input for the visually optimized tone scaling, the method disclosed in U.S. Pat. No. 5,633,511, issued May 27, 1997, to inventors H.-C Lee, et al. These four points are called the far-left, the left, the right, and the far-right point. The code values between the left point and the right point correspond to the sub-range of the input code values. This sub-range corresponds the most important body parts which are examined. In the case of Lspine image, this sub-range corresponds to bone patterns of Lspine. The far-left point and the far-right point are used to roll off both ends (the toe and the shoulder) of the tone scale curve. This will prevent the tone scale curve producing a hard clipping in the displayed image.

Figure 10A:
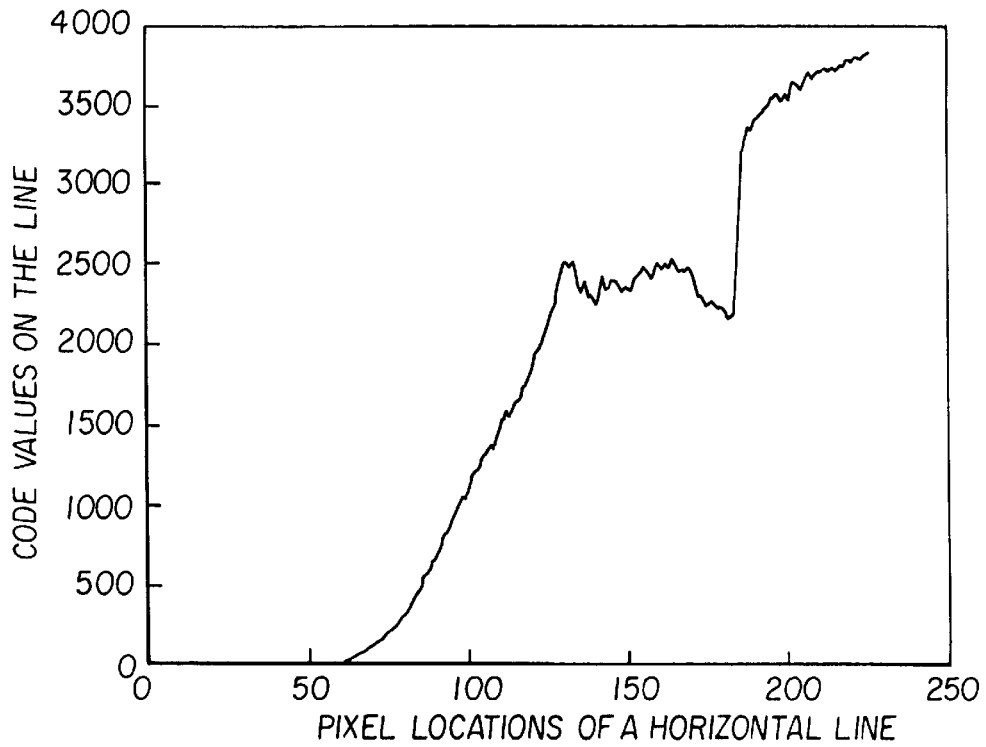
FIG. 10($a$) is a graphical view showing the image profile of a horizontal line of one Lspine image processed by the visually optimized tone scale.
Figure 10B:
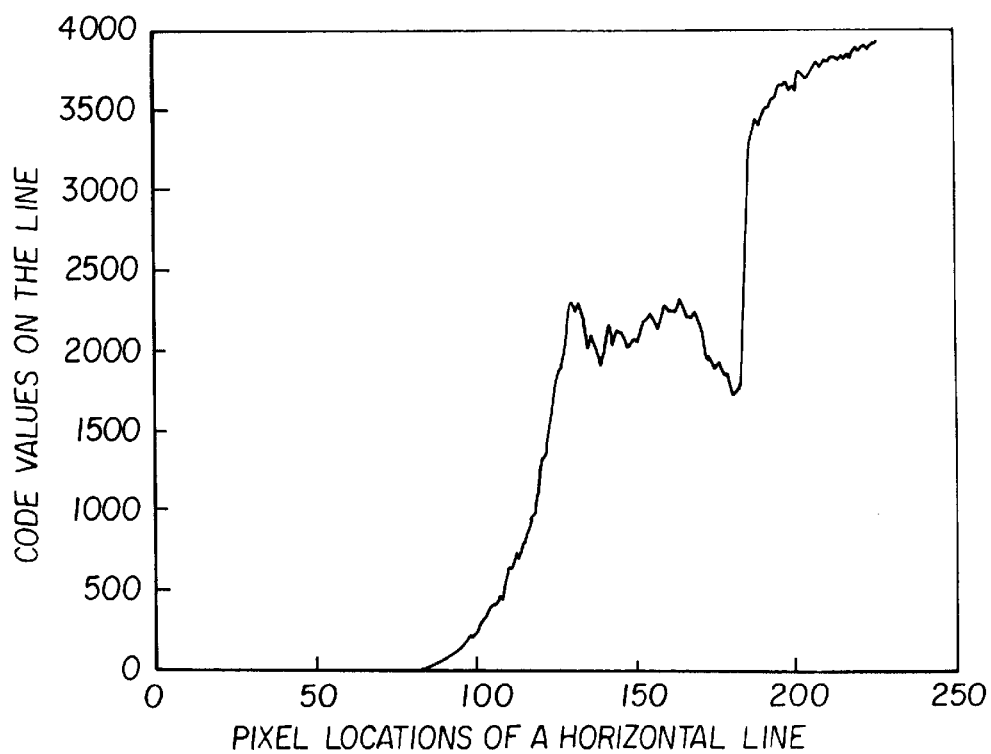

These four points are input to the visually optimized tone scale algorithm to generate a tone scale curve that maps the code values to an output display, such as radiographic film. FIG. 10 shows the image profiles of a horizontal line from two resultant images, separately. FIG. 10(a) shows the image profile of a horizontal line of a Lspine image which is processed by the method disclosed in U.S. Pat. No. 5,633,511 using the activity histogram from the level-crossing measurements. FIG. 10(b) shows the image profile of the horizontal line of a Lspine image which is processed by the method in the present invention using the image pattern histogram. It displays the advantage of the method using the image pattern histogram. FIG. 10(b) shows a higher contrast of bone area of the Lspine image than in FIG. 10(a).

The invention has been described in detail with particular reference to certain preferred embodiments thereof, but it will be understood that variations and modifications can be effected within the spirit and scope of the invention.

Parts List 30 image acquisition system
32 image enhancement system
34 image display
300 digital computer
310 memory
312 input device
314 display 316 central processing unit
318 output device
320 control/data bus
322 transportable storage medium drive
324 transportable storage media

What is claimed is:

1. A method of automatically locating intervertebral disks of lumbar spine in digital images comprising the steps of:

provipding a digital image having intervertebral disks of lumbar spine;

applying a set of directional ridge filters;

searching for a pair of disk space ridge points;

computing the image pattern histogram;

constructing the tone scale curve for the provided digital image from the image pattern histogram; and applying the tone scale curve to said provided digital image to produce an output image.

2. The method of claim 1 wherein said directional ridge filter is designed by:

determining a horizontal ridge filter which is the waveform function in x-direction and a constant in y-direction;

determining a directional ridge filter by rotating the said horizontal ridge filter with certain increments in plural directions; and determining the said ridge filter parameters based on the physical pixel spacing size.

3. The method of claim 1 wherein said searching step includes:

generating a line along the maximum response direction of the said ridge filter;

searching for another ridge point on the said line (in both directions);

locating an ending ridge point by determining the absolute difference of the angular directions of the starting and the ending points below a certain threshold;

determining a profile vector of the line connecting the starting and the ending ridge points;

checking the local maxima conditions, that is, for a valid pair of disk space ridge points, the starting and the ending ridge points should be local maxima of the said profile vector;

checking the local minimal conditions, that is, for a valid pair of disk space ridge points, the minimum of the said profile does not occur at the boundary (ridge points);

checking the range condition 1 of the boundary ridge points, that is, for a valid pair of disk space ridge points, the maximum of the differential boundary changes, (differential boundary change is defined as the difference of the code value of one ridge point and the point next to it), should be a fraction of the code value range of the said profile vector;

checking the range condition 2 of the boundary ridge points, that is, for a valid pair of disk space ridge points, the differential change of ridge points, which is defined as the difference of the code values of two ridge points (the starting and the ending ridge points), should be a fraction of the code value range of the said profile vector; and checking the convex condition, that is, for a valid pair of disk space ridge points, the points between the starting and the ending ridge points are below the line that connects the two ridge points on the said profile.

4. The method of claim 1, wherein said image pattern histogram is constructed from the searched valid disk space ridge points and the points between the said profile vector.

* * * * *